United States Patent [19]

Chartrain et al.

[11] Patent Number: 5,464,762
[45] Date of Patent: Nov. 7, 1995

[54] ASYMMETRIC BIOREDUCTION OF 6-BROMO-2-TETRALONE TO (S)-6-BROMO-2 TETRAOL BY TRICHOSPORON CAPITATUM

[75] Inventors: Michel M. Chartrain, Westfield; Jayanthi Reddy, Scotch Plains; David M. Tschaen, Holmdel, all of N.J.

[73] Assignee: Merck & Co., Inc., Rahway, N.J.

[21] Appl. No.: 265,176

[22] Filed: Jun. 24, 1994

[51] Int. Cl.[6] .................. C12P 7/22; C12P 41/00
[52] U.S. Cl. ............. 435/156; 435/280; 435/911
[58] Field of Search .................... 435/280, 156, 435/911

[56] References Cited

PUBLICATIONS

ATCC Catalogue of Filamentous Fungi, pp. 79, 440 (1991).
ATCC Catalogue of Yeasts, pp. 46, 96, 164 (1990).

Primary Examiner—Irene Marx
Assistant Examiner—S. Saucier
Attorney, Agent, or Firm—Francis P. Bigley; Mark R. Daniel; Joseph F. DiPrima

[57] ABSTRACT

Stereospecific (S)-6-bromo-2-tetraol is a key intermediate in the chemical synthesis of the chiral drug candidate, MK499, a ventricular arrythmias suppressant. The yeast strain *Trichosporon capitatum* (MY 1890) was employed for the bioconversion of 6-bromo-2-tetralone to the corresponding alcohol.

3 Claims, 1 Drawing Sheet

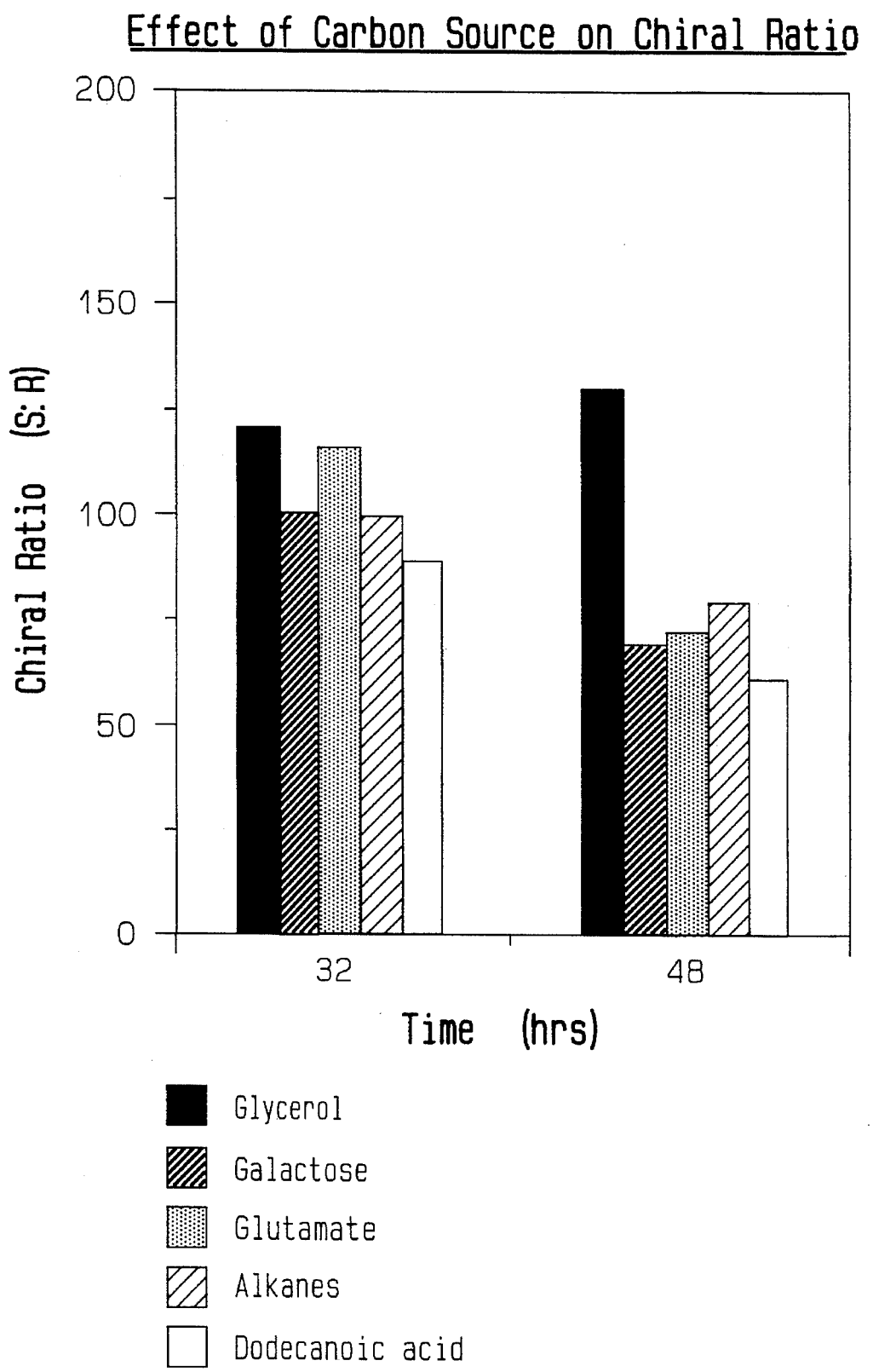

ASYMMETRIC BIOREDUCTION OF 6-BROMO-2-TETRALONE TO (S)-6-BROMO-2 TETRAOL BY TRICHOSPORON CAPITATUM

BACKGROUND OF THE INVENTION

The antiarrhythmic pharmaceutically active compound, (+)-N-[ 1'-(6-Cyano-1,2,3,4-tetrahydro-2-napthalenyl)-3, 4dihydro-4-hydroxyspiro[ 2H-1-benzopyran-2,4'-piperidin] yl]methanesulfonamide (Formula I) is a potent potassium channel blocker for treatment of life-threatening ventricular arrhythmia and the prevention of sudden cardiac death. It is currently undergoing intensive clinical trials. In order to support the on-going clinical study, a practical, asymmetric bioreduction of 6-bromo-2-tetralone (Formula II) to (S)-6-bromo-2-tetraol (Formula III) is highly desirable. The synthesis of the chiral alcohol of Formula I is challenging because it contains a unique spiro-fused ring system and two remote chiral centers which must be controlled independently.

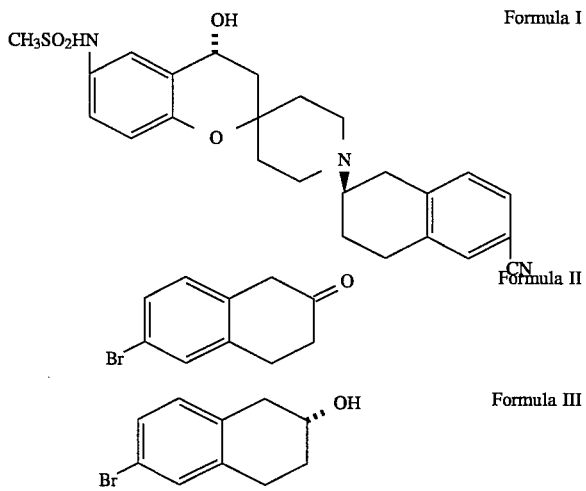

As an alternative to asymmetric chemical synthesis of the intermediate (S)-6-bromo-2-tetraol, a bioconversion process, employing the yeast strain *Trichosporon capitatum* (MY 1890) and the substrate 6-bromo-2-tetralone is presented. This asymmetric bioreduction process yields to rapid process improvements, including rebalancing the cultivation medium and optimizing the bioconversion conditions. The use of 5 to 10% (v/v) ethanol to solubilize the substrate was found to be critical in maintaining high optical purity of the (S)-6-bromo-2-tetraol. Glucose present in the cultivation medium was found to have a negative effect on optical purity and was replaced by glycerol. When this process was scaled up to production size quantities, (S)-6-bromo-2-tetraol with an enantiomeric excess greater than 98% was obtained.

SUMMARY OF THE INVENTION

A culture medium which is effective to support growth of and production of *Trichosporon capitatum* (MY 1890) (ATCC 74312) and which is effective to support production of (S)-6-bromo-2-tetraol is presented. In addition, a method for the bioconversion of 6-bromo-2-tetralone to (S)-6-bromo-2-tetraol is presented.

BRIEF DESCRIPTION OF THE DRAWINGS

FIG. 1 is a bar graph representing the effect of carbon source on the optical purity (chiral ratio) of the β-tetraol produced by bioreduction of the β-tetralone, employing *Trichosporon capitatum* MY 1890. The chiral ratio data presented here are those obtained when employing washed cells (as described in Example 6 herein) harvested after 32 and 48 hours of cultivation, respectively.

DETAILED DESCRIPTION OF THE INVENTION

A culture medium comprising *Trichosporon capitatum* (MY 1890) which is effective to support the assymetric bioreduction of 6-bromo-2-tetralone to (S)-6-bromo-2-tetraol is presented. In addition, a method for the bioconversion of (S)-6-bromo-2-tetralone to 6-bromo-2-tetraol is presented.

The present invention is related to a general fermentation process for the conversion of 6-bromo-2-tetralone by yeast cells. The process of the present invention is demonstrated using a strain of *Trichosporon capitatum* (MY 1890)(ATCC 74312). As will be appreciated by one of ordinary skill in the art, the process of the present invention has a more general application to cultivation of other strains of yeast and the production of other stereospecific products and is not limited simply to the production of (S)-6-bromo-2-tetraol.

The present invention is directed to a fermentation process which employs a readily prepared culture medium. Culture medium as used herein is defined as a mixture which supports the growth of yeast cells, which mixture contains ingredients such as peptone, soy peptone, and yeast extract powder.

One preferred formulation of the medium of this invention is as follows:

Glycerol 60 g/l;

Hysoy Peptone 50 g/l (obtained Sheffield Incorporated, located in Norwich, N.Y.;

Yeast extract 20 g/l (obtained from Difco, located in Detroit, Mich.); and

*Trichosporon capitatum* was added at about 2% v/v to the medium. Good results will be achieved when the *Trichosporon capitatum* is added at between 0.2% to 5% v/v.

It should be understood that the precise amounts of ingredients provided above may be optimized, or modified so long as no new components are introduced. The key aspect of the medium is its ability to support growth of *Trichosporon capitatum* (MY 1890) and thereby the production of (S)-6-bromo-2-tetraol useful for pharmaceutical production.

Glucose is normally provided as a carbon source, however, for the purpose of this bioconversion, glucose was shown to have a negative effect in maintaining high optical purity and was replaced by glycerol.

It will be understood by those of ordinary skill in the art that by the expression "enantiomeric excess" or "ee" is meant, the percent excess of one enantiomeric form over the other. If the ratio of the enantiomers is A:B, then EE=(A−B)/(A+B)*100.0.

The following Examples, demonstrate production and use of the medium of this invention to support the inoculum development and growth of *Trichosporon capitatum* (MY 1890) and the bioconversion of 6-bromo-2-tetralone to (S)-6-bromo-2-tetraol.

EXAMPLE 1

The substrate, 6-bromo-2-tetralone may be prepared via a four step synthesis. In Step 1, synthesis of the cyanopiperidone ketone is accomplished using the following reaction sequence

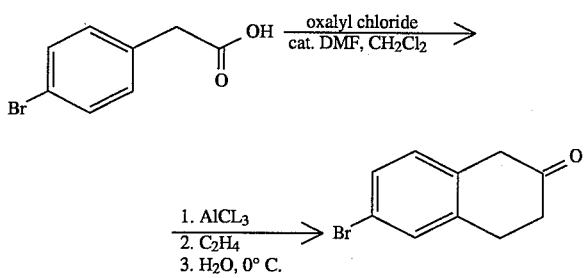

The synthesis of 6-bromo-2-tetralone is accomplished by dissolving 4-bromophenylacetic acid in methylene chloride and dimethyl formamide, under nitrogen. Oxalyl chloride is added and the mixture is stirred under a positive nitrogen atmosphere to produce the 4-bromo-phenylacetyl chloride, at a yield which typically is better than 99%.

The ethylene addition reaction is accomplished by first reacting $AlCl_3$ with the acid chloride to produce the alluninum addition salt, and then adding the ethylene gas. The addition and ring closure reactions are allowed to proceed until approximately 2% of the starting material remains (by HPLC). The reaction is then quenched with the addition of cold (0° C.) water.

EXAMPLE 2

Frozen seed cultures were prepared using a lyophilized tube of *Trichosporon capitatum* (MY 1890). The seed and production medium were made up of 30 g/L Sabouraud Dextrose (Difco). The buffer contained 5 g/l of MES (N-morpholino ethanesulfonic acid, obtained from Sigma Chemical Co.) and 10 g/l of glucose. Prior to use the frozen cell culture was stored at −70° C. The culture was thawed at room temperature and used to inoculate a 250 ml Erlenmeyer flask containing 50 ml of seed medium incubated on an orbital shaker (220 rpm) at 28° C.

After 48 hours of cultivation, 30 mg of 6-bromo-2-tetralone dissolved in 1 ml of ethanol was added to the flask to initiate the bioconversion. The flasks containing the substrate were aerobically incubated on an orbital shaker (220 rpm) at 28° C. for an additional 24 hours. For extraction of the 6-bromo-2-tetraol, an equal volume of ethyl acetate was added to the broth and after through mixing the sample was centrifuged for 10 minutes at 5000 rpm in a Beckman model TJ-6 centrifuge. The supernatant was dried down in a fume hood and resuspended in 2 ml of methanol The extract in methanol was then spotted on a TLC plate for identification of the reaction product.

EXAMPLE 3

Production Stage—A 2-l Erlenmeyer flask containing 500 ml of medium was inoculated with 10 ml of the first stage seed. The culture was aerobically incubated for 36 hours on an orbital shaker (220 rpm) at 28° C.

Scale Up—A 23-l Chemap fermentor containing 16 liters of production medium was inoculated with 500 ml of the 2-l Production Stage that was grown for 36 hours. The fermentor was agitated at 220 rpm (DO controlled at 30%), aerated with 6 liters of air per minute, and operated at 28° C. with a back pressure of 0.6 bar. On-line monitoring of the bioreactor consisted of dissolved oxygen, pH, temperature, back pressure, agitation, air flow, and respiratory activity (oxygen uptake rate and carbon dioxide evolution rate were analyzed by mass-spectrometry).

Bioconversion Procedure—The culture was harvested by centrifuging the broth at 3000 rpm in a Sorvall RC-5B Centrifuge for 20 minutes. The cells were resuspended in MES buffer at pH 5.0. The bioconversion was initiated by adding 600 mg/l of 6-bromo-2-tetralone to the cell suspension in buffer. The substrate, 6-bromo-2-tetralone, was dissolved in a 2% v/v solution of ethanol. After 12–16 hours, the broth was extracted with two volumes of ethylacetate and the extract assayed for the 6-bromo-2-tetraol by reverse phase HPLC.

Biomass Measurement—Biomass determinations were performed off-line samples by measuring dry cell weights.

Glucose Measurement—Residual glucose concentrations in the broth were measured in off-line samples using a Beckmann Glucose Analyzer.

High Performance Liquid Chromatgraphy—To determine the concentration of 6-bromo-2-tetralone and the product, 6-bromo-2-tetraol in the samples, a reverse phase column was employed. A Rainin HPLC with a Zorbax RX-C8 HPLC column (4.6 mm×25 cm), Dynamax autosampler, Dynamax absorbance detector, and two Rainin pumps for solvent delivery were used for HPLC analysis via a computer-control program on a Macintosh Classic II. The 6-bromo-2-tetralone concentrations were quantified by an isocratic method employing acetonitrile and 0.1% phosphoric acid 50/50 (v/v) mobile phase, at a flow rate of 1.5 ml/min and UV detection at 220 nm. The 6-bromo-2-tetraol had a retention time of 4.9 minutes and the 6-bromo-2-tetralone had a retention time of 6.5 minutes.

Chiral Assay—Quantification of the S and R enantiomers of 6-bromo-2-tetraol was carried out using a Spectra Physics HPLC equipped with a UV detector. A Chiralcel OD column (250×4.6 mm) obtained from Chiral Technologies was used with a mobile phase of 98% hexane and 2% isopropanol at a flowrate of 0.6 ml/min. The retentime time of the (S)-6-bromo-2-tetraol was 25.9 minutes and the retention time of the (R)-6-bromo-2-tetralone was 27.5 minutes.

Thin Layer Chromatography—Kiesel precoated silica gel 60 tin layer chromatography plates F254 were spotted with two applications of 3 ul each. The spotted plates were then eluted with 94% methylene chloride, 5% methanol and 1% ammonium hydroxide.

EXAMPLE 4

Table 1 lists several strains of yeast which were able to convert the ketone to the alcohol. Of these, the four strains where able to provide a chiral ration (S:R) which was greater than or less than unity. Based on these results, the yeast strain *Trichosporon capitatum* (MY 1890), which produced a chiral ratio of 6:1 (ee of 71%), appeared to be the most efficient strain.

TABLE 1

Production of 6-BROMO-2 TETRAOL and Chirality Results

| Microorganism | S:R Ratio |
| --- | --- |
| Yarrowia lipolytica (ATCC 48436) | 1:1 |
| Pichia strasburgensis (MY 1614) | 3:1 |
| Candida kruisii (MY 1807) | 1:3 |
| Candida milleri (MY 1826) | 1:1 |
| Candida citrus (MY 1818) | 2:1 |

TABLE 1-continued

Production of 6-BROMO-2 TETRAOL and Chirality Results

| Microorganism | S:R Ratio |
|---|---|
| *Tricosporon capitatum* (MY 1890) | 6:1 |
| *Rhodotorulla rubra* (M 1) | 1:1 |
| *Candida famata* (MY 1888) | 1:1 |
| *Hansenula fabianii* (MY 1496) | 1:1 |

EXAMPLE 5

When *Trichosporon capitatum* (MY 1890) was cultivated in Sabouraud Dextrose broth, there was very little glucose utilized during the first 24 hours, after which there was rapid utilization. After 36 hours of cultivation, cells from a 2 l Erlenmeyer flask were used for bioconversion. The bioconversion was initiated by adding 600 mg/l of 6-bromo-2-tetralone in 3% (v/v) ethanol to the broth. The bioconversion proceeded very rapidly within the first two hours and then slowed. Most of the bioconversion was completed within the first 8 hours. Final 6-bromo-2-tetraol concentrations of 200 mg/l were obtained.

EXAMPLE 6

When 36 hour-old cells from the production Stage of Example 2 were harvested and resuspended or "washed" in MES buffer at pH 6.0, and the bioconversion initiated (S)-6-bromo-2-tetraol was formed at a rate of 120 mg/l/hr. This represented an almost two fold increase when compared to control cells. For the "washed" cells, more than 90% of the bioconversion was completed within the first 6 hours. The S:R ratio remained unchanged on washing the cells. That is, "washing" the cells resulted in an improvement in the bioconversion rate as well as a much cleaner final product.

When the pH of the medium was examined, pH of 6.0 using MES buffer was found to be optimal for the bioconversion process. However, pH had no effect on the S:R enantiomeric ratio.

The effect of culture age on chiral ratio indicated that cells harvested at 36, 48 and 72 hours resulted in much lower chiral ratios. An S:R ratio of 20:1 (ee=90.4) was obtained when the cells were harvested at 16 hrs and 24 hrs.

EXAMPLE 7

The substrate, 6-bromo-2-tetralone, is highly insoluble in water and needs to be dissolved in a suitable solvent before being added to the cell suspension. An extremely poor bioconversion rate of 40 mg/l/hr and a poor S:R ratio of 2:1 (ee=33.33) was obtained when the substrate was added to 24 hour-old "washed" cells without dissolving the substrate in a solvent first. Solvents such as ethanol, dimethyl sulfoxide and methanol were studied. Similar bioconversion rates of 120 mg/l/hr were obtained using a 2%, 3%, 5% and 10% ethanol concentration (v/v). (v/v stands for volume of ethanol used to volume of cell suspension). However, the 5% and 10% ethanol bioconversions resulted in higher S:R enantiomeric ratios of 30:1 (ee=93.5).

Substantially lower chiral ratios were obtained using methanol and dimethyl sulfoxide.

EXAMPLE 8

The medium used in the studies of Examples 2 to 7 contained 30 g/l of Sabouraud dextrose (20 g/l glucose, 10 g/l neopeptone). This medium yielded poor chiral ratios. Neopeptone (10 g/l) was replaced with peptone (10 g/l) and yeast extract (4 g/l). Seven different peptones were tested. The chiral ratios obtained using these seven different media is shown in Table 2. The medium containing hysoy peptone had the highest chiral S:R ratio at the three cultivation times tested. The difference in bioconversion yield was not significant when the different media were compared. Based on these results, hysoy peptone (Sheffield), yeast extract (Difco) and glucose were selected as the growth medium constituents.

The medium components were then optimized in terms of stereospecificity and yield of the bioconversion using statistical experimental design. The production medium was rebalanced at the 2-1 shake-flask scale, employing a Box Behnken factorial design. Computational data analysis of the data showed that glucose had a negative effect on yield and chiral ratios at all concentration of yeast extract and hysoy peptone. Higher yeast extract concentration had a slight negative effect on the chiral ratios. The older the culture, the better the chiral ratio and the yield. Chiral ratios up to 100:1 (ee 99%) were obtained in the medium containing 5 g/L glucose, 5 g/l yeast extract, and 24 g/L peptone.

Additional studies showed that best yields and best chiral rations (greater than 100:1) were obtained when using 0 g/l glucose. Glycerol, glactose, sodium glutamate, mixtures of alkanes and dodecanoic acid were tested as alternative carbon sources. FIG. 1 shows the chiral ratios obtained with cells harvested at 32 hours and 48 hours from a 2 l shake flask. Medium containing glycerol as the carbon source yielded the highest chiral ratios for 6-bromo-2-tetraol (greater than 150:1; ee=99%).

These studies indicated that the optimum growth medium would contain 60 g/l of glycerol, 50 g/l of hysoy peptone and 20 g/l of yeast extract. This medium produced (S)-6-bromo-2-tetraol having an optical purity greater than 99%. A yield of roughly 500 mg/l of the desired product was obtained when the broth was charged with 600 mg/l of the substrate.

TABLE 2

S:R Ratios for Peptones at Different Cultivation Times

| Peptone Source | Culture Age | | |
|---|---|---|---|
|  | 17 hr | 22 hr | 41 hr |
| Hysoy Peptone | 36 | 40 | 38 |
| Casamino Acids | 30 | 25 | 13 |
| Peptonized Milk | 20 | 10 | 9 |
| Sheftone C | 6 | 17 | 15 |
| Sheftone D | 9 | 12 | 7 |
| Soya Meal | 13 | 20 | 13 |
| Sabouraud | 28 | 20 | 9 |

EXAMPLE 9

The optimum temperature for bioconversion using whole broth was determined by studying the bioconversion at 28°, 32°, 37° and 42° C. The initial bioconversion rate at 37° C. was 1.25 g/l/hr and this was higher than the rates at other temperatures. There appeared to be product degradation at 42° C. resulting in a lower bioconversion rate as well as final yield.

What is claimed is:

1. A method of using a medium which comprises 60 g/l of glycerol, 50 g/l of soy peptone, and 20 g/l of yeast extract for the production of (S)-6-bromo-2-tetraol with an optical purity greater than 98%, the method comprising:
   (a) cultivating *Trichosporon capitatum* (MY 1890) (ATCC 74312) in the medium;
   (b) mixing 6-bromo-2-tetralone into the medium; and
   (c) recovering the (S)-6-bromo-2-tetraol produced.

2. The method of claim 1 wherein the 6-bromo-2-tetralone is dissolved in ethanol before being added to the medium.

3. The method of claim 2 wherein the concentration of ethanol ranges from 5% to 10% calculated on a volume to volume basis.

* * * * *